United States Patent [19]

Boxer

[11] 3,987,787

[45] Oct. 26, 1976

[54] PROCESS AND DEVICE FOR ALLEVIATION OF MUSCULAR AND NON-MUSCULAR PAIN AND DISCOMFORT

[75] Inventor: Steve Boxer, 13617 Sherman Way, Van Nuys, Calif. 91405

[73] Assignee: Steve Boxer, Van Nuys, Calif. 91405

[22] Filed: Feb. 14, 1975

[21] Appl. No.: 549,858

Related U.S. Application Data

[63] Continuation-in-part of Ser. No. 393,974, Sept. 4, 1973, Pat. No. 3,866,597.

[52] U.S. Cl. .................. 128/1 R; 128/268; 128/329 A; 128/333

[51] Int. Cl.$^2$ .................. A61B 17/34

[58] Field of Search .......... 128/268, 253, 1 R, 2 W, 128/329 A, 2.1 C, 333, 95

[56] References Cited

UNITED STATES PATENTS

| | | | |
|---|---|---|---|
| 102,262 | 4/1870 | Herrick | 128/333 |
| 2,817,336 | 12/1957 | Kravitz et al. | 128/253 |
| 3,062,212 | 11/1962 | Kravitz et al. | 128/253 |
| 3,136,314 | 6/1964 | Kravitz | 128/253 |
| 3,590,821 | 7/1971 | Orlandini | 128/239 A |
| 3,625,202 | 12/1971 | Oyoshirhara | 128/24.3 |
| 3,866,597 | 2/1975 | Boxer | 128/1 R |
| 3,886,939 | 6/1975 | Boxer | 128/268 |

*Primary Examiner*—Aldrich F. Medbery

[57] ABSTRACT

A process and device for alleviation of muscular and non-muscular pain and discomfort by applying a device containing one or more small rigid objects to produce pressure at designated points of a person's body without puncturing the person's skin.

10 Claims, 3 Drawing Figures

PROCESS AND DEVICE FOR ALLEVIATION OF MUSCULAR AND NON-MUSCULAR PAIN AND DISCOMFORT

This application is a continuation in part of application Ser. No. 393,974, filed Sept. 4, 1973, and now U.S. Pat. No. 3,866,597.

BACKGROUND OF THE INVENTION

1. Field of the Invention

This invention relates to a new and improved process and device for alleviation of muscular and non-muscular pain and discomfort.

2. Prior Art

Applicant is unaware of any prior art disclosing the application of one or more small rigid objects of varying shapes adhering to a plaster backing which alleviates muscular and non-muscular pain and discomfort when applied to various points of a person's body without puncturing the person's skin.

SUMMARY OF THE INVENTION

The invention comprises the combination of at least one or more small rigid objects affixed to an adhesive base material, such as conventional surgical plaster or the like. The objects may range in size from about 1 millimeter to about 6 millimeters and may be made from any suitable rigid material that retains its rigidity under moderate pressure. The base material of each device preferably has a minimum size of about 1 inch wide and about 3 inches long.

The process for alleviating muscular pain and discomfort includes affixing a minimum of 6 of the small objects to the area of muscular discomfort, without puncturing the skin. This may be done by using a single device having at least 6 small objects affixed to it, or alternatively, by using a minimum of 6 units of a device having a single small object affixed to it. The use of a minimum of 6 objects is critical.

The process for alleviating non-muscular pain and discomfort includes applying a minimum of one unit of the device, each having at least one small object affixed thereon, to each of a minimum of four trigger points or zones of a person's body, without puncturing the person's skin.

It is, therefore, an object of this invention to provide a process and device for symptomatic relief of muscular and non-muscular pain and discomfort.

Another object of this invention is to provide a process and device which a person can use by himself without special training.

A further object of this invention is to provide a process and device which are relatively inexpensive and easy to use.

These and other objects will be more readily understood by reference to the accompanying drawing in which FIG. 1 is a plan view of an embodiment of my invention.

Figure 1:
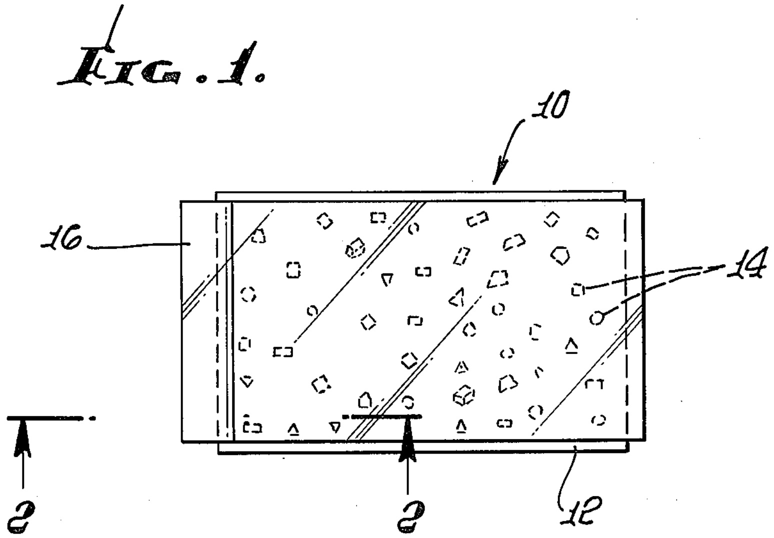
Figure 2:
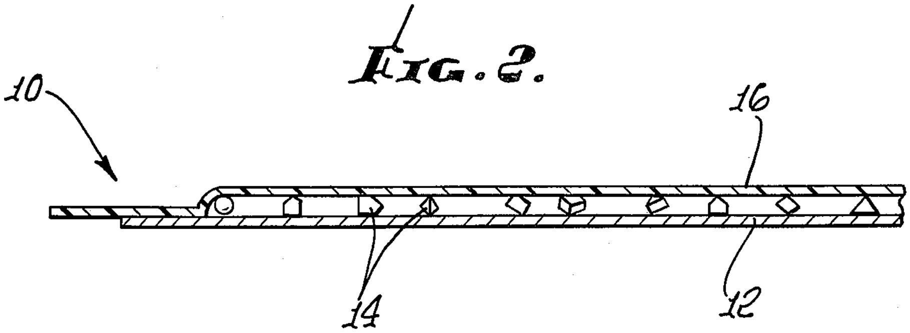
FIG. 2 is a section taken along line 2—2 of FIG. 1.
Figure 3:
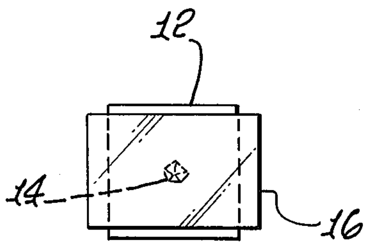
FIG. 3 is an enlarged section of a portion of FIG. 1 showing an individual object.

The device 10 is constructed by using a base material 12 having adhesive properties such as surgical plaster or the like. A single rigid object 14 is then affixed to base material 12.

For a device 10 having a plurality of small objects 14, one or more rigid objects 14 is affixed to the surface of the base material 12 in a random arrangement or in a symmetrical fashion. Although not necessary, it is preferable to have a cover 16 of any suitable material placed over the objects. The cover 16 preferably may be of some adhesive material which can be readily peeled off. The objects 14 may range in size from about 1 to about 6 millimeters in thickness. The relatively small size of the objects 14 is critical.

The objects 14 may take various forms. The objects 14 may be polygonal in form, such as rhombic, cubic, pentagonal, hexagonal, octagonal, and the like, or even irregularly shaped, as well as being circular. The objects 14 may be solid or hollow provided that the objects remain sufficiently rigid to maintain their shape and their pressure when applied to an area of a person's body.

Moreover, various forms of the objects 14 may be used within one device, or they may be all the same form. Thus, the device 10 may have a plurality of one shape such as cubic, of the objects 14, or one device 10 may have a plurality of objects 14, each of which is different in shape from the other. Thus, a device 10 may have one cubic object 14, one rhombic object 14, one pentagonal object 14, one hexagonal object 14, one irregularly shaped object 14, and other different forms.

In use for muscular pain and discomfort, the device 10 is applied to a person's body so that at least six of the objects 14 produces pressure against the area of muscular pain and discomfort of a person's body for a suitable period of time. A suitable period of time may range from 2 to 4 hours up to one day or more, during which time the device 10 will alleviate muscular pain and discomfort.

In use for non-muscular pain and discomfort, the device 10, having one or more of the objects 14, is applied to each of a minimum of four trigger points or zones of a person's body for a suitable period of time, ranging from two hours to one day or more. Application of the device 10 to each of at least four trigger points or zones is critical. Such application will result in alleviation of the non-muscular pain and discomfort.

Although I have described by invention in detail with reference to the accompanying drawing illustrating preferred embodiments of my invention and with reference to preferred embodiments of a process using the device 10, it is understood that numerous changes in the details of construction and arrangement of parts may be made without departing from the spirit and scope of the invention as hereinafter claimed.

I claim:

1. A device for alleviating non-muscular pain and discomfort of a person's body by applying said device to at least four of the body's trigger points and trigger zones without puncturing said person's skin, comprising:

means for applying pressure to said trigger points and trigger zones, including, a base material having non-medicated adhesive properties, and at least one rigid pressure applying object affixed to said base material and adapted for contact with said trigger points and trigger zones, said object being non-elongated and of a shape so as to not easily puncture said person's skin, said object being located between said base material and the person's skin.

2. A device according to claim 1 in which said object has a thickness ranging from about 1 millimeter to about 6 millimeters.

3. A device for alleviating muscular pain and discomfort of a person's body by applying said device to the body area having muscular pain and discomfort, without puncturing said person's skin, comprising:

means for applying pressure to selected points of a person's body, including a base material having non-medicated adhesive properties, and at least six rigid objects affixed to said base material, and adapted for contact with said points, said objects being non-elongated and of a shape so as to not easily puncture said person's skin, said objects being located between said base material and the person's skin.

4. A device for alleviating muscular pain and discomfort of a person's body by applying said device to the body area having muscular pain and discomfort, without puncturing said person's skin, in a minimum of six units of said device, comprising:

means for applying pressure to selected points of a person's body, including a phase material having non-medicated adhesive properties, and at least one rigid object affixed to said base material, and adapted for contact with said points, said object being non-elongated and of a shape so as to not easily puncture said person's skin, said object being located between said base material and the person's skin.

5. A process for alleviating non-muscular pain and discomfort of a person's body by applying a device consisting of non-medicated adhesive material with at least one small rigid object affixed to said adhesive material in contact producing pressure to at least four of the trigger zones and trigger points of a person's body associated with said nonmuscular pain, without puncturing said person's skin, and maintaining said device in position for a suitable length of time.

6. A process according to claim 5 in which said device is maintained in position for at least 2 hours.

7. A process for alleviating muscular pain and discomfort of a person's body by applying a device consisting of non-medicated adhesive material with at least six small rigid objects affixed to said non-medicated adhesive material in contract producing pressure on the skin at selected trigger points of a person's body associated with said muscular pain and discomfort without puncturing said person's skin, and maintaining said device in position for a suitable length of time.

8. A process according to claim 7 in which said device is maintained in position for at least 2 hours.

9. A process for alleviating muscular pain and discomfort of a person's body applying at least six devices each consisting of non-medicated adhesive material with a least one small rigid object affixed to said adhesive material in contact producing pressure on the skin at selected trigger points of a person's body associated with muscular pain and discomfort without puncturing said person's skin, and maintaining said device in position for a suitable length of time.

10. A process according to claim 9 in which said devices are maintained in position for at least 2 hours.

* * * * *